US010729808B2

(12) United States Patent
Setton et al.

(10) Patent No.: US 10,729,808 B2
(45) Date of Patent: Aug. 4, 2020

(54) STERNUM REPLACEMENT IMPLANT

(71) Applicant: I.CERAM, Limoges (FR)

(72) Inventors: Daniel Setton, Limoges (FR); Fabrice Fiorenza, Limoges (FR); François Bertin, Limoges (FR); Frank Sturtz, Limoges (FR); Eric Denes, Limoges (FR); Delphine Donnez, Limoges (FR)

(73) Assignee: I.CERAM, Limoges (FR)

( * ) Notice: Subject to any disclaimer, the term of this patent is extended or adjusted under 35 U.S.C. 154(b) by 0 days.

(21) Appl. No.: 15/735,997

(22) PCT Filed: Jun. 22, 2016

(86) PCT No.: PCT/EP2016/064482
§ 371 (c)(1),
(2) Date: Dec. 13, 2017

(87) PCT Pub. No.: WO2016/207255
PCT Pub. Date: Dec. 29, 2016

(65) Prior Publication Data
US 2018/0177914 A1 Jun. 28, 2018

(30) Foreign Application Priority Data
Jun. 23, 2015 (FR) .................................... 15 55761

(51) Int. Cl.
*A61L 27/10* (2006.01)
*A61L 27/56* (2006.01)
(52) U.S. Cl.
CPC ............ *A61L 27/105* (2013.01); *A61L 27/56* (2013.01)

(58) Field of Classification Search
None
See application file for complete search history.

(56) References Cited

U.S. PATENT DOCUMENTS

| 3,314,420 | A | * | 4/1967 | Smith | ................. | A61F 2/30767 |
| | | | | | | 623/23.3 |
| 3,919,723 | A | * | 11/1975 | Heimke | ............... | A61K 9/2009 |
| | | | | | | 623/23.57 |
| 4,878,914 | A | * | 11/1989 | Miwa | .................. | A61F 2/30767 |
| | | | | | | 623/23.56 |
| 2002/0147451 | A1 | * | 10/2002 | McGee | ..................... | A61F 2/28 |
| | | | | | | 606/62 |
| 2004/0220615 | A1 | * | 11/2004 | Lin | .................... | A61B 17/0401 |
| | | | | | | 606/232 |
| 2004/0230312 | A1 | * | 11/2004 | Hanson | ................. | A61F 2/4261 |
| | | | | | | 623/21.12 |

(Continued)

FOREIGN PATENT DOCUMENTS

| FR | 2823674 | 10/2002 | | |
| FR | 2823674 A1 | * 10/2002 | ............. | A61L 27/10 |

OTHER PUBLICATIONS

Amini et al. "Bone Tissue Engineering: Recent Advances and Challenges", Crit Rev Biomed Eng 2012; 40(5); pp. 363-408. (Year: 2012).*

(Continued)

*Primary Examiner* — Carlos A Azpuru
*Assistant Examiner* — Casey S Hagopian
(74) *Attorney, Agent, or Firm* — Duane Morris LLP; Gregory M. Lefkowitz; Jason M. Nolan

(57) ABSTRACT

The invention relates to a sternum replacement implant.

9 Claims, 2 Drawing Sheets

(56) References Cited

U.S. PATENT DOCUMENTS

2008/0195204 A1\* 8/2008 Zhukauskas ............ A61F 2/08
623/13.14

OTHER PUBLICATIONS

Neuhuber et al. "Anatomy and Blood Supply of the Sternum" Deep Sternal Wound Infections, Springer 2016, pp. 7-13. (Year: 2016).\*
Machine translation of FR 2823674 A1, Oct. 2002. (Year: 2002).\*
Kazmier et al. "Bacterial adhesion to alumina ceramic versus cobalt-chrome femoral head", 49th Annual Meeting of the Orthopaedic Research Society, Feb. 2003, New Orleans, LA (Year: 2003).\*
Milisavljevic et al.: "Sternum Resection and Chest Wall Reconstruction with Metaacrilate Implant in Tuberculosis", Jul. 6, 2012 (Jul. 6, 2012), XP055263856, Retrieved from the Internet <URL:http://www.ncbi.nlm.nih.gov/pmc/articles/PMC3693342/> [retrieved on Apr. 8, 2016].
Milos Stojkovic et al: "Reverse modeling and solid free-form fabrication of sternum implant", Australasian Physical and Engineering Sciences in Medicine., vol. 33, No. 3, Sep. 7, 2010 (Sep. 7, 2010), AU, pp. 243-250, XP055264212, ISSN: 0158-9939, DOI: 10.1007/s13246-010-0029-1.

\* cited by examiner

STERNUM REPLACEMENT IMPLANT

CROSS-REFERENCE TO RELATED APPLICATIONS

This application is a § 371 national stage entry of International Application No. PCT/EP2016/064482, filed Jun. 22, 2016, which claims priority to French Patent Application No. 1555761, filed Jun. 23, 2015, the entire contents of which are incorporated herein by reference.

The present invention relates to a sternum replacement implant.

In the case of unique lesions or severe infections, a total sternectomy may be performed. This is the case of radiation-induced cancers of the sternum (and bone metastases on the sternum) and of postoperative mediastinum (POM), which occurs following a postoperative complication in the sternum following heart surgery.

Therefore, sternum replacement implants are sought.

To date, two solutions are available to the surgeon, particularly cardiovascular or orthopaedic specialists. The sternum may be replaced by a titanium prosthesis, but it involves a high risk of infection and causes artefacts impeding X-rays, while representing a significant psychological burden for the patient. It is also possible to perform the construction during the operation of a custom-made piece of bone cement (PMMA) with the addition of metal fastenings, but here again with a risk of infection and a prolongation of the duration of the procedure, coupling difficulty due to the lack of holes and heat released during shaping with burn risks.

Moreover, secondary osteointegration of the implant within a time-frame compatible with physiological requirements is sought.

DETAILED DESCRIPTION

Figure 1:
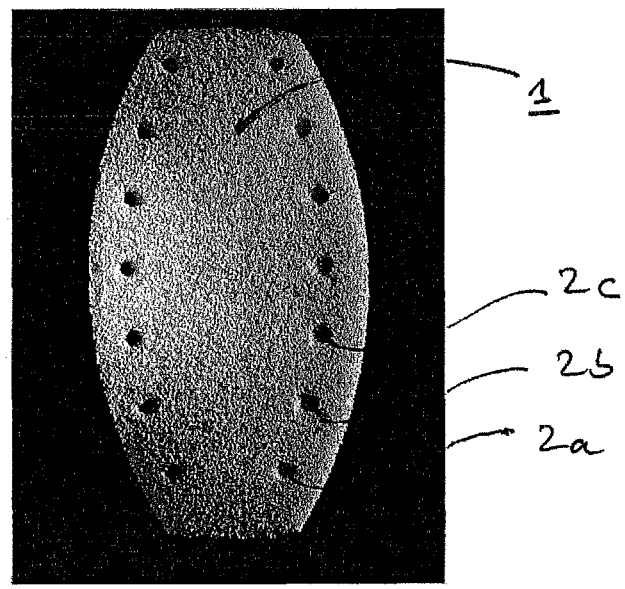
FIG. 1 is a top view of a sternum implant as described herein.

The invention relates to a sternum replacement implant based on alumina ceramic.

The ceramic, based on alumina $Al_2O_3$, is advantageously porous. This alumina ceramic is known per se but it may be used doped with certain other materials such as Zirconia.

The porosity (open and interconnected) of this ceramic may particularly be between 40 and 80%, preferably between 60 and 70%, advantageously approximately 65%.

The pore size is typically from 200 to 600 μm, preferably 400 μm.

The porosity/pore size is measured by mercury porosimetry. The porosity is defined by the difference between the volume occupied by the pores over the total volume, the total volume between the sum of the volume of the pores and of alumina. The mass of alumina being defined by the volume and the density, by weighing the sample and knowing the total volume thereof, it is possible to determine by differential the pore volume and therefore the (open) porosity.

Porous alumina, the constituent material of the implant according to the invention, enables secondary osteointegration of the implant at approximately 3 months.

The mechanical compressive strength is advantageously between 20 and 60 MPa, advantageously greater than 40 MPa.

Any known method for preparing porous alumina may be used, particularly by impregnation of a foam, pre-sintering at a temperature greater than 1200° C., superimpregnation with a slip, and sintering at a temperature greater than 1600° C.

A method comprising the following steps may particularly be used:

(A) providing a porogenic material (such as foam, for example polyurethane foam, serving to adjust the porosity and the pore size in particular) and impregnation of the porogenic material with a suspension of alumina ceramic particles (alumina slip) optionally in a mixture with various organic additives such as binders, plasticisers and dispersants;

(B) drying in an oven;

(C) low-temperature heat treatment (below 700° C.) to remove the foam and the organic constituents from the suspension; followed by (D) sintering at a temperature greater than 1500° C.

The method described in the patent application FR2823674 may advantageously be used.

In particular, the ceramic matrix according to the invention may be prepared using the method described therein. In the preferred embodiment, after implementing the first two phases as described above (phases A, B), the porous ceramic piece is pre-sintered at a temperature greater than 1200° C., giving same greater cohesion (phase C'). The cycle is continued with a further steeping of the piece in a further suspension of ceramic particles (phase E). The viscosity of this concentrated suspension is controlled by means of various organic auxiliaries (binders, plasticisers, dispersants), in order to be suitable for homogeneous impregnation of the pre-sintered porous piece. After further drying in an oven (phase B') and pyrolysis of the organic auxiliaries of the suspension (phase C), the ceramic piece is finally sintered at a temperature greater than 1600° C. according to a suitable cycle (phase D').

This super-impregnation method reinforces the mechanical properties of the sintered ceramic and multiplies the strength thereof by a factor of 2, particularly the compressive breaking stress.

Such a ceramic is available from the applicant, under the reference Ceramil®.

The desired shape may be given to the matrix by machining or by shaping directly during sintering.

FIG. 1 is a top view of the implant (1) according to the invention. The implant has lateral holes (2a, 2b, 2c), for example between 0.8 and 4 mm in diameter. Machining, particularly ultrasonic machining, may be performed to produce the holes. The implant equipped with holes may therefore subsequently be sutured to the costal cartilages. The implant thereby offers surgeons additional practicality by means of the holes produced which enables simplified securing of the implant.

Figure 2:
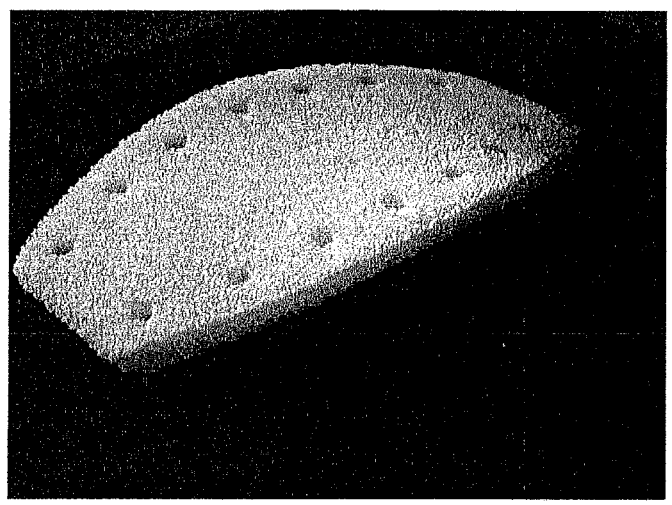
FIG. 2 is a top, perspective view of a sternum implant as described herein.

FIG. 2 is a further view of the implant (2) according to the invention. The implant is in the form of a curved ovoid sheet, which has an anatomical geometry. This makes it possible to fill the excised area while respecting the physiology of the rib cage.

Figure 3:
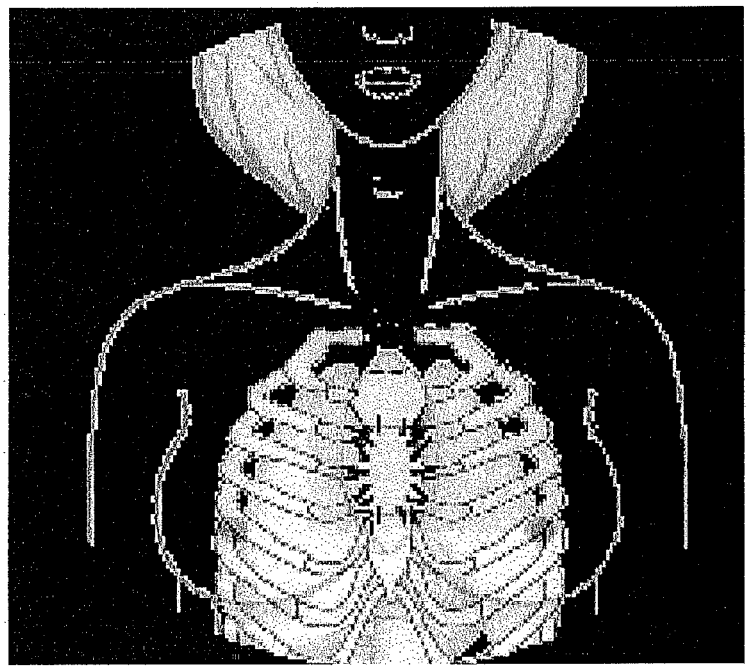
FIG. 3 is a schematic view showing a sternum implant as described herein sutured in position following implantation.

After having performed anatomical referencing, the surgeon makes a skin incision comprising the path and the point of entry of the biopsy, cuts the ribs and makes an excision followed by a one-piece ablation of the tumour. The surgeon fits the implant, performs the suturing required and covers the implant with a flap of the pectoralis major. The implant in position is shown in FIG. 3.

The ceramic sternum according to the invention offers full biocompatibility enabling long-term bone integration. The non-use of metal pieces makes it possible to perform X-rays without artefacts and thereby benefit from quality imaging so as to enhance clinical follow-up. The use of the implant according to the invention also makes it possible to save operating time, which reduces the risk of infection, the studies indicating that prolonging an operation by one hour multiplies the risk of infection by two.

The overall impact for the patient is also lessened. Indeed, the "natural" integration of the implant according to the invention limits the psychological effects of such an operation. The osteointegration facilitates the acceptance of the implant within the body and gives a plasticity to the chest after operation.

The ceramic sternum also makes it possible to ensure reproducibility of the operation; according to one embodiment, the sternum according to the invention is available in the form of a range of implants, with for example 3 implant sizes.

The invention claimed is:

1. A Sternum replacement implant made of an alumina ceramic, wherein the implant has a curved ovoid sheet shape, and comprises lateral holes for suturing to costal cartilages.

2. Implant according to claim 1, wherein the alumina ceramic has a porosity by volume of 45 to 75% and a pore size of 200 to 600 µm.

3. Implant according to claim 1, wherein the alumina ceramic is obtained by impregnation of a foam, pre-sintering at a temperature greater than 1200° C., superimpregnation with a slip, and sintering at a temperature greater than 1600° C.

4. Implant according to claim 1, wherein the alumina ceramic is doped.

5. A Sternum replacement implant consisting of an alumina ceramic, wherein the implant has a curved ovoid sheet shape and wherein the implant has a plurality of lateral holes configured for suturing to costal cartilages.

6. Implant according to claim 5, wherein the alumina ceramic has a porosity by volume of 45 to 75% and a pore size of 200 to 600 µm.

7. Implant according to claim 5, wherein the alumina ceramic is obtained by impregnation of a foam, pre-sintering at a temperature greater than 1200° C., superimpregnation with a slip, and sintering at a temperature greater than 1600° C.

8. A sternum replacement implant consisting of a doped alumina ceramic, wherein the implant has a curved ovoid sheet shape and a plurality of holes along each lateral side of the implant, each of the holes configured for suturing to costal cartilages.

9. Sternum replacement implant consisting of an alumina ceramic, wherein the implant has a curved ovoid sheet shape and a plurality of holes along each lateral side of the implant, each of the holes configured for suturing to costal cartilages, and wherein the alumina ceramic has a porosity by volume of 45 to 75% and a pore size of 200 to 600 µm.

* * * * *